(12) United States Patent
Woodruff

(10) Patent No.: US 12,605,254 B2
(45) Date of Patent: Apr. 21, 2026

(54) EXPANDABLE INTERVERTEBRAL CAGE IMPLANT

(71) Applicant: Robert Woodruff, Rapid City, SD (US)

(72) Inventor: Robert Woodruff, Rapid City, SD (US)

( * ) Notice: Subject to any disclaimer, the term of this patent is extended or adjusted under 35 U.S.C. 154(b) by 135 days.

(21) Appl. No.: 18/653,281

(22) Filed: May 2, 2024

(65) Prior Publication Data

US 2024/0374398 A1 Nov. 14, 2024

Related U.S. Application Data

(60) Provisional application No. 63/464,783, filed on May 8, 2023.

(51) Int. Cl.
*A61F 2/44* (2006.01)
*A61F 2/46* (2006.01)
*A61F 2/30* (2006.01)

(52) U.S. Cl.
CPC ............ *A61F 2/447* (2013.01); *A61F 2/4611* (2013.01); *A61F 2002/30537* (2013.01)

(58) Field of Classification Search
CPC .......... A61F 2/44; A61F 2/442; A61F 2/4425; A61F 2/4455; A61F 2/446; A61F 2/4465; A61F 2/447; A61F 2002/443; A61F 2/4611; A61F 2002/30537
See application file for complete search history.

(56) References Cited

U.S. PATENT DOCUMENTS

| | | | | |
|---|---|---|---|---|
| 7,819,921 | B2 * | 10/2010 | Grotz .................... | A61F 2/4611 |
| | | | | 606/90 |
| 8,628,576 | B2 * | 1/2014 | Triplett ................. | A61F 2/4465 |
| | | | | 623/17.13 |
| 8,663,329 | B2 * | 3/2014 | Ernst ...................... | A61F 2/442 |
| | | | | 623/17.15 |
| 8,940,052 | B2 * | 1/2015 | Lechmann ............ | A61F 2/4425 |
| | | | | 623/17.11 |
| 9,055,981 | B2 * | 6/2015 | Lamborne .......... | A61B 17/7065 |
| 10,881,531 | B2 * | 1/2021 | Berry .................... | A61F 2/4611 |
| 2010/0209184 | A1 * | 8/2010 | Jimenez ................... | E05D 1/02 |
| | | | | 403/291 |

(Continued)

OTHER PUBLICATIONS

Globus Medical, Inc., Expandable Technology, Sable Spacer Product Page, 2024, 9 pages, https://www.globusmedical.com/expandabletechnology/sable/.

(Continued)

*Primary Examiner* — Ellen C Hammond
(74) *Attorney, Agent, or Firm* — David R. Heckadon; Gordon Rees Scully Mansukhani LLP

(57) ABSTRACT

An expandable intervertebral cage, having: a top plate with rotatable leaves thereon; a bottom plate with rotatable leaves thereon; front and rear wedges; and a deployment mechanism that moves the front or rear wedges to rotate the leaves on the top and bottom plates into a deployed position that increases the width of the intervertebral cage. The deployment mechanism also moves the wedges to push the top and bottom plates farther apart thereby increasing the height of the intervertebral cage, or moves one of the wedges while keeping the other wedge stationary to vary a lordosis angle for the intervertebral cage.

10 Claims, 9 Drawing Sheets

(56)  References Cited

U.S. PATENT DOCUMENTS

| | | | |
|---|---|---|---|
| 2012/0083889 A1* | 4/2012 | Purcell | A61F 2/442 |
| | | | 623/17.16 |
| 2012/0123546 A1* | 5/2012 | Medina | A61F 2/447 |
| | | | 623/17.16 |
| 2013/0158663 A1* | 6/2013 | Miller | A61F 2/4455 |
| | | | 623/17.16 |
| 2014/0052253 A1* | 2/2014 | Perloff | A61F 2/4425 |
| | | | 623/17.15 |
| 2015/0073555 A1* | 3/2015 | To | A61F 2/442 |
| | | | 623/17.16 |
| 2017/0007422 A1* | 1/2017 | Perloff | A61F 2/442 |
| 2018/0193164 A1* | 7/2018 | Shoshtaev | A61F 2/4425 |
| 2020/0352738 A1* | 11/2020 | Berry | A61F 2/4455 |
| 2022/0015923 A1* | 1/2022 | Shoshtaev | A61F 2/4611 |
| 2023/0114356 A1* | 4/2023 | Kang | A61F 2/30749 |
| | | | 623/17.16 |
| 2023/0172726 A1* | 6/2023 | Krawiec | A61B 34/30 |
| | | | 623/17.15 |
| 2024/0307191 A1* | 9/2024 | Siccardi | A61F 2/4455 |
| 2025/0032270 A1* | 1/2025 | Berry | A61F 2/4455 |
| 2025/0213369 A1* | 7/2025 | Weiman | A61F 2/4425 |

OTHER PUBLICATIONS

Life Spine, Inc., Prolift Expandable Spacer System, 2020, 5 pages, https://lifespine.com/prolift/.

Spineology, Inc., Elite Expandable Interbody Fusion System, 2023, 3 pages, https://www.spineology.com/products/elite-expandable.

* cited by examiner

100

104

102

100

102

104

EXPANDABLE INTERVERTEBRAL CAGE IMPLANT

RELATED APPLICATION

The present application claims priority to U.S. Provisional Patent Application Ser. No. 63/464,783, of same title, filed May 8, 2023, the entire disclosure of which is incorporated herein by reference in its entirety for all purposes.

TECHNICAL FIELD

The present invention relates to intervertebral implants in general, and to intervertebral expandable cage implants in particular.

BACKGROUND OF THE INVENTION

Intervertebral cages have been used in spinal fusion cases for decades. Placement through a posterior or transforaminal approach is more recent but still has been a mainstay of spine surgery for the last 20 to 30 years at least. However, the size of these cages has been limited by the anatomical restrictions imposed by the boney and neural structures. Kambin's triangle is formed by traversing the nerve root medially, the caudal pedicle inferiorly, and exiting the nerve root superiority. Insertion requires retraction of the nerves to open up enough space to safely place the cage in between the 2 vertebra within the disc space. Unfortunately, the anatomy limits the size of the cage both in width and in height. Therefore, static cages often are somewhat undersized in order to fit within the disc space or endplate violation is risked if a larger cage is placed.

Because of the above problems, expandable intervertebral interbody cages are being used at increasing rates in spinal surgery. The general idea behind an interbody cage is that the cage is placed within the disc space to separate the vertebra, thereby restoring more normal alignment, helping to decompress the nerves, and increasing fusion rates. An expandable cage has the advantage of being able to be placed in its collapsed form through a small surgical opening and then have the cage increase to its final height within the disc space, thereby avoiding some of the risks of the static cage placement. It also has the added benefit of allowing for a greater amount of lordosis to be achieved with the cage, at least initially. Restoring lordosis is one of the most important things to be achieved during an operation. However, the act of expanding the cage can exert significant pressure on the boney endplates and, in some cases, the endplates can break because the pressure is being exerted on a relatively small area of the bone. This leads to loss of the lordotic correction that had been initially gained, thereby leading to possible pinching of the nerves again and increased stresses felt by the surrounding structures and discs, leading to a higher rate of future surgery.

There are a multitude of cage options that expand in height. Examples of such systems include the Globus Medical Sable™ system, the Life Spine Prolift® system, and the Spineology Elite™ system. Cages that expand in height solve the insertion problem. However, these cages are still limited by the neural elements in their width and most cages are no more than 10 mm wide. Because of this, when expanded, these cages can in some cases exert more pressure on the endplates than their static counterparts.

A few intervertebral cages have attempted to tackle the deficiency of cages that expand only in height by developing designs that increase in width as well. The theoretical benefits of a cage that expands in both width and in height are significant. The biggest benefit of such systems are that they increase the surface area of the cage to allow pressure to be spread out and thereby decrease the chance of endplate violation, while maintaining the correction that was achieved at the time of surgery.

The problem with current designs that both expand in height and width is that as the width increases, the surface areas at the top and bottom of the cage (i.e.: the actual contact area where the cage touches against the vertebrae above and below) remains unchanged. The space between the endplates is just spread apart. Basically, as these cages expand, the top portion simply has parts that move laterally away from one another. The problem with this is that as these current designs expand, a void develops within the middle of the cage itself. As a result, these expandable designs rely on injecting bone graft material to fill the void. Unfortunately, this approach is unreliable at best. This is because the bone that does fill the void is not strong or structural and provides no immediate support. In addition, numerous studies show that it is the bone graft material that is placed around the cage that leads to the bulk of the fusion mass, rather than the bone graft material that is filling the cage.

In short, what is desired is an intervertebral cage that would instead increase its surface contact area with the vertebrae both above and below the cage when the cage is deployed. Increasing the contact surface area between the top/bottom of the cage and the vertebrae above/below the cage would provide enhanced stability as well as spread the forces out over a much larger area, decreasing endplate fracture as the cage is expanded. Moreover, it may also be desirable for such an expandable cage to not have an expanding interior void that increases in size during expansion. Such an expanding void would require additional bone graft material being inserted into the cage after it has been expanded. Finally, a further desirable aspect of a new expandable intervertebral cage would be to have separate degrees of expansion at the front and back of the cage as this would allow for adjustment for custom lordosis for each individual patient.

SUMMARY OF THE INVENTION

In preferred aspects, the present system provides an expandable intervertebral cage, having: a top plate; a pair of rotatable leaves on opposite sides of the top plate; a bottom plate; a pair of rotatable leaves on opposite sides of the bottom plate; a front wedge; a rear wedge; and a deployment mechanism. The deployment mechanism moves either or both of the front or rear wedges to rotate the leaves on the top and bottom plates into a deployed position. This is preferably done by moving four blocks that are located within the cage, with each block being positioned adjacent to a rotatable leaf. In short, the wedges push against the blocks and the blocks push against the leaves (thereby moving the leaves into their deployed positions). Preferably, both the wedges and the blocks all have angled contact surfaces to facilitate this movement.

The deployed position of the leaves on the top plate is preferably coplanar with the top plate and the deployed position of the leaves on the bottom plate is preferably coplanar with the bottom plate. As such, the leaves rotate from a vertical non-deployed position to a horizontal deployed position. By rotating the leaves outwardly during deployment, the width of the vertebral contact surfaces of the intervertebral cage is increased. Further movement of the wedges under the control of the deployment mechanism can be used to push the top and bottom plates apart, thereby increasing the height of the intervertebral cage.

Although wedges are preferred, it is to be understood that the present invention encompasses all manner of deployment systems that rotate the leaves into their deployed position in which the deployment of the leaves increases the effective surface area of the present intervertebral cage. The present invention is not therefore limited only to moving wedge systems for deploying the leaves.

In preferred aspects, the deployment mechanism uses differently sized screw adjustment mechanisms to move the front and rear wedges independently of one another. As a result, moving one wedge while keeping the other wedge stationary varies the angle between the top and bottom plates, thereby varying the lordosis angle of the intervertebral cage. As such, the present cage can be inserted with its top and bottom plates initially being parallel to one another, and then moved to non-parallel positions corresponding to different lordosis angles.

In other preferred aspects, the present system provides a method of deploying an intervertebral cage in an intervertebral space, comprising: inserting the present expandable intervertebral cage into an intervertebral space; and then engaging the deployment mechanism to move either or both of the front or rear wedges to rotate the leaves on the top and bottom plates into a deployed position. This preferred method may also include moving the front and rear wedges independently to vary a lordosis angle for the intervertebral cage. This preferred method may also include moving either or both of the front or rear wedges to push against one or more blocks disposed within the intervertebral cage, wherein each of the blocks are positioned against one of the leaves such that movement of the blocks moves the leaves into the deployed position. This motion increases the width of the intervertebral cage. In addition, moving either or both of the front or rear wedges to push against the blocks can also move the top and bottom plates father apart, thereby increasing the height of the intervertebral cage.

The deployment mechanism itself may include a screw-type device that can engage and rotate a first diameter screw mechanism to move the front wedge and to engage and rotate a second diameter screw mechanism to move the rear wedge. In preferred aspects, the screw-type device may be passed through an aperture in the first wedge to engage with the second wedge. In preferred aspects, each of the front and rear wedges comprise screw adjustment mechanisms. Most preferably, these screw adjustment mechanisms have different diameters such that it is possible to first reach through the larger diameter screw aperture mechanism and adjust the deployment of the opposite far side of the cage, and then use a larger screw aperture mechanism to adjust the deployment of the near side of the cage. As such, only one surgical access path is required to separately adjust the front and back of the cage.

During deployment, the front wedge moves towards the rear of the cage when deployed and the rear wedge moves towards the front of the cage. In an alternative formulation, the expansion mechanism can be fixed to a certain lordotic angle. In this case, the screw mechanism would simultaneously move the anterior wedge posteriorly and the posterior wedge anteriorly to achieve the desired expansion. In alternate designs, the front wedge can be a pair of front wedges positioned side-by-side and the rear wedge can be a pair of rear wedges positioned side-by-side as well.

A first advantage of the present system is that it expands the surface area (i.e.: the contact area between the cage itself and the vertebrae above and below) when deployed, thus providing enhanced vertebral stability. With current ingrowth technology being used at the vertebral endplate, this increases the surface area for the fusion of the endplate to the cage itself, thereby increasing fusion surface area.

A second advantage of the present system is that it does not develop a large central void (which would otherwise have to be filled with bone graft material) within the cage when the present cage is fully deployed.

A third advantage of the present system is that its vertical deployment dimension can be separately adjusted at the front and back of the cage, such that it can be deployed in a way that actually matches the lordosis of the patient in which it is being used.

DETAILED DESCRIPTION OF THE DRAWINGS

The present system provides an intervertebral cage that is expandable both vertically and horizontally. Vertical expansion provides support against the vertebrae above and below the cage. Horizontal expansion widens the surface area of the device contacting each of the vertebrae above and below the cage. As such, a very stable intervertebral cage support system is provided.

When expanded vertically, the front and rear portions of the device may be expanded to different heights. As such, the present intervertebral cage can be best fit to the particular lordosis of the patient in which the cage is installed. Preferably as well, the separate deployment of the front and rear portions of the cage may be carried out through the same surgical access path. In short, only one insertion or pathway is required to access both the front and rear deployment systems.

Figure 1A:
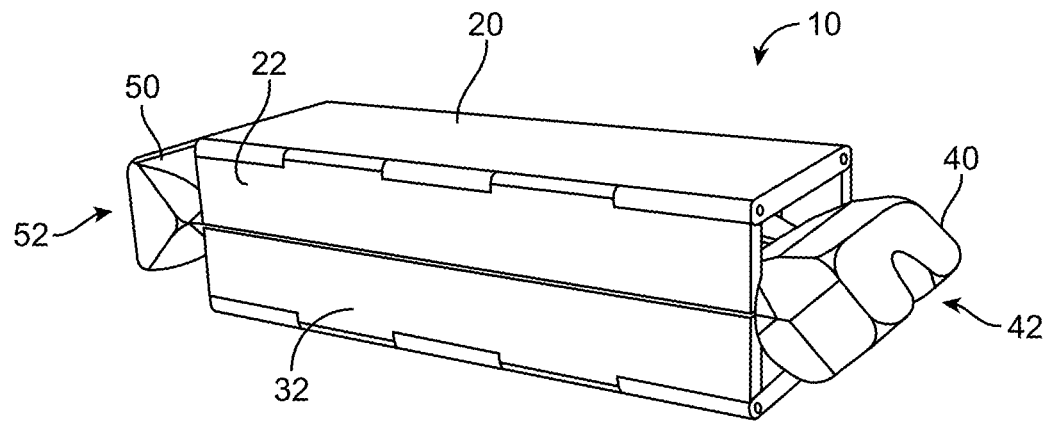
FIG. 1A is a front perspective view of an embodiment of the present intervertebral cage prior to deployment, showing the folded against the side of the case, and showing the front and rear wedges.
Figure 1B:
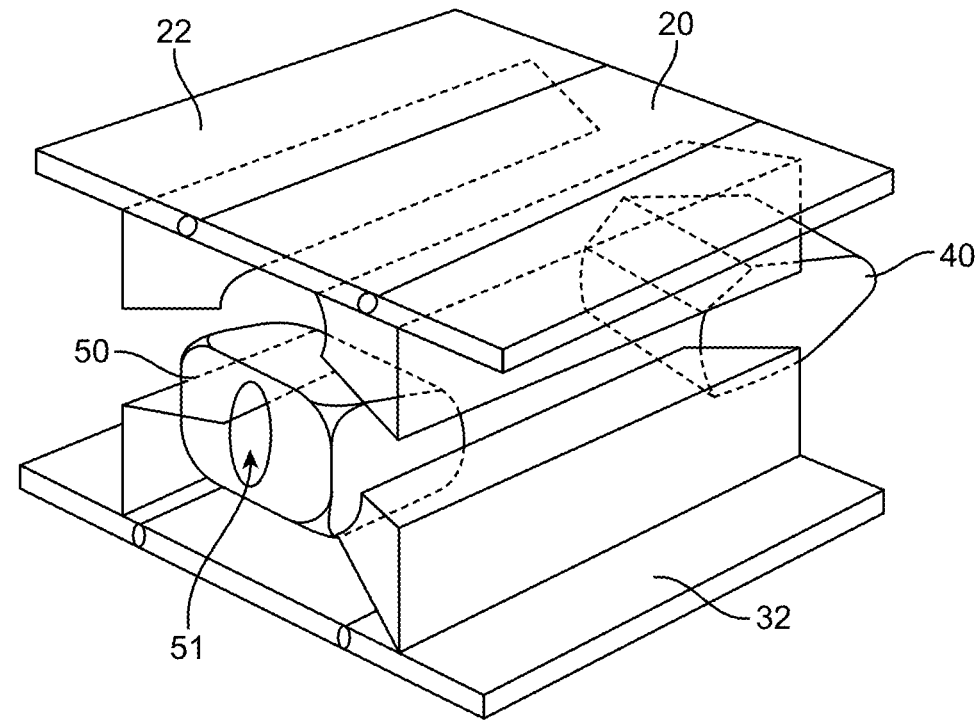
FIG. 1B is a rear perspective view of the embodiment of FIG. 1.

Referring first to FIGS. 1A and 1B, the present system provides an expandable intervertebral cage 10, comprising: a top plate 20; a pair of rotatable leaves 22 on opposite sides of top plate 20; a bottom plate 30; a pair of rotatable leaves 32 on opposite sides of bottom plate 30; a front wedge 40; and a rear wedge 50. The present system also includes a deployment mechanism that moves either or both of the front or rear wedges 40 and 50 to rotate the leaves 22 and 32 on the top and bottom plates 20 and 30 into their deployed position. The deployment mechanism may include a screw mechanism 42 in front wedge 40 for deploying front wedge 40, and a screw mechanism 52 in rear wedge 50 for deploying rear wedge 50. The present deployment mechanism can also preferably include the elongated screw-type device or devices (100 in FIG. 9) that is adapted to interlock with screw mechanism 42 and with screw mechanism 52. For example, the present deployment mechanism can include a screwdriver 100 that is inserted through aperture 51 in rear wedge 50 to reach and then interlock with and turn screw mechanism 42 in front wedge 40. Once front wedge 40 has been moved to its desired position by rotating screw mechanism 42, (i.e.: front wedge 40 moves backwards a short distance towards the center of cage 10), the screwdriver device can be removed and a different size of screwdriver end can be used to engage with and rotate screw mechanism 52 in rear wedge 50 thereby moving rear wedge to its desired position (i.e.: rear wedge 50 moves forwards a short distance towards the center of cage 10).

This screwdriver-type device (described further below) may include a larger outer screw device that engages with the rear screw mechanism 52 and a smaller screw device that engages with the front screw mechanism 42. The smaller screw device is passed through the center of the larger screw device such that it engages with wedge 40 at the front of the cage, and when rotated, deploys (i.e. moves) wedge 40 at the front of the cage. Next, the larger screw device engages with wedge 50 at the rear of the cage, and deploys wedge 50 at the rear of the cage. As understood herein, the deployment mechanism thereby includes any and all devices that moves either or both of the front or rear wedges 40 and 50 into positions that rotate the leaves 22 and 32 on the top and on the bottom plates 20 and 30 into their deployed position. As also understood herein, the deployment mechanism also includes systems which do not require wedges. Rather, any system for deploying the present leaves is understood to be included within the scope of the present system.

Figure 2:
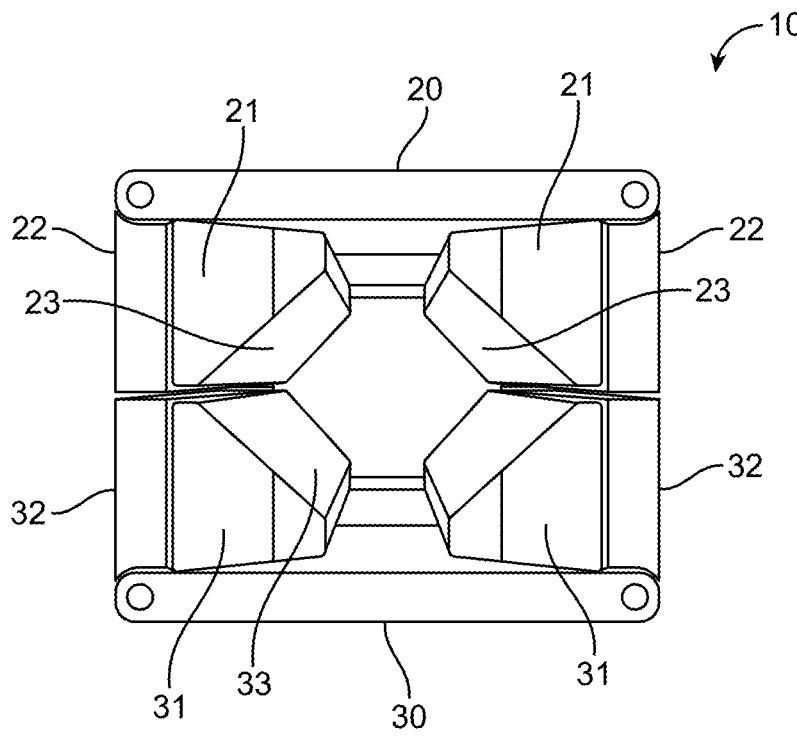
FIG. 2 is a front view corresponding to FIGS. 1A and 1B, but with the front and rear wedges removed to show the interior structure of the intervertebral cage.
Figure 3:
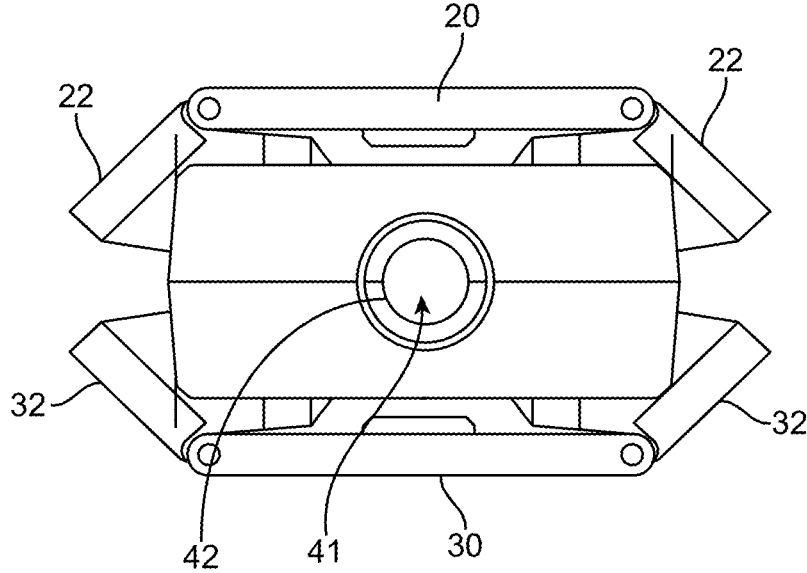
FIG. 3 is a front view as the leaves are deployed.

FIG. 2 is a front view corresponding to FIGS. 1A and 1B, but with the front and rear wedges removed to show the interior structure of the intervertebral cage 10. As can be seen, prior to deployment, leaves 22 and 32 are in a vertical orientation. As can also be seen, four blocks 21 and 31 are also provided inside cage 10. One of the four blocks is positioned adjacent to each of the four leaves (i.e.: blocks 21 are positioned adjacent to leaves 22 and blocks 31 are positioned adjacent to leaves 32. As wedges 40 and 50 are moved (inwardly towards the center of the case), they push against and move blocks 21 and 31. The movement of blocks 21 and 32 in turn causes the movement and deployment of leaves 22 and 32. FIG. 3 is a front view as the leaves are deployed.

In preferred aspects, the front and rear wedges 40 and 50 have angled surfaces thereon, and blocks 21 and 32 also have angled surfaces 23 and 33 thereon. As such, blocks 21 and 31 are moved by the angled surfaces of the front and rear wedges 40 and 50 pushing against the angled surfaces 23 and 33 of the blocks. Specifically, as can be seen angled surfaces 23 and 33 are angled inwardly towards the center of the intervertebral cage.

Figure 4:
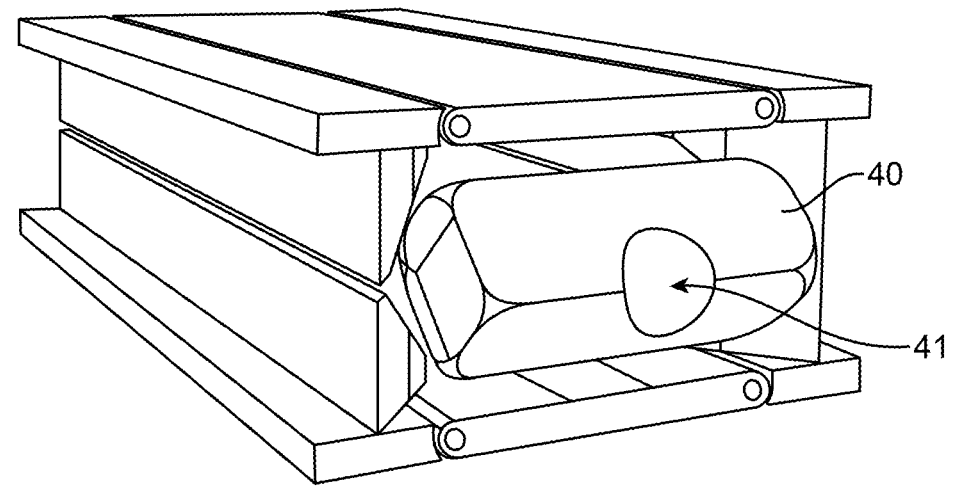
FIG. 4 is a perspective view of the intervertebral cage with the leaves fully deployed, showing the increased width of the intervertebral cage.
Figure 5:
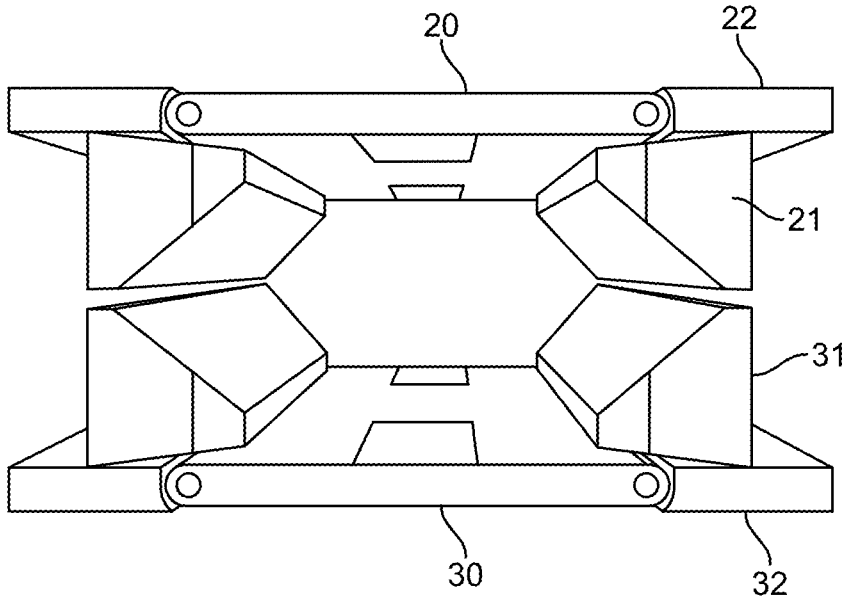
FIG. 5 is a front view corresponding to FIG. 4, but with the front and rear wedges removed to show the interior structure of the intervertebral cage.

FIGS. 4 and 5 show the leaves 22 and 32 in their fully deployed positions. As can be seen, the deployed position of leaves 22 on top plate 20 is coplanar with the top plate and the deployed position of leaves 32 on bottom plate 30 is coplanar with the bottom plate. As such, leaves 22 and 32 rotate from a vertical non-deployed position (FIGS. 1A and 1B) to a horizontal deployed position (FIGS. 4 and 5). As can be appreciated, deploying the leaves on the top and bottom plates increases the width of the intervertebral cage.

As stated above, the deployment mechanism moves the front and rear wedges 40 and 50 independently of one another (for example by rotating screw mechanism 42 to move front wedge 40 and later by rotating screw mechanism 52 to move rear wedge 50).

Figure 6:
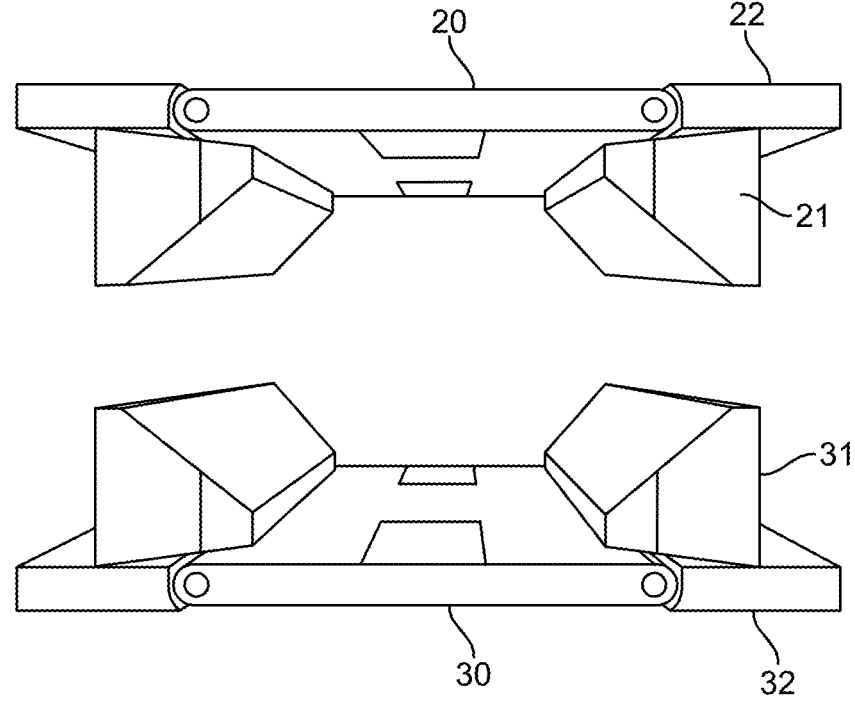
FIG. 6 is a front view corresponding to FIG. 5, but showing the top and bottom plates being pushed further apart, thereby increasing the height of the intervertebral cage.

Next, as seen in FIG. 6, the deployment mechanism can moves front and rear wedges further inwardly to push against blocks 21 and 31, and thereby push the top and bottom plates 20 and 30 farther apart. This effectively increases the height of the intervertebral cage.

Figure 7:
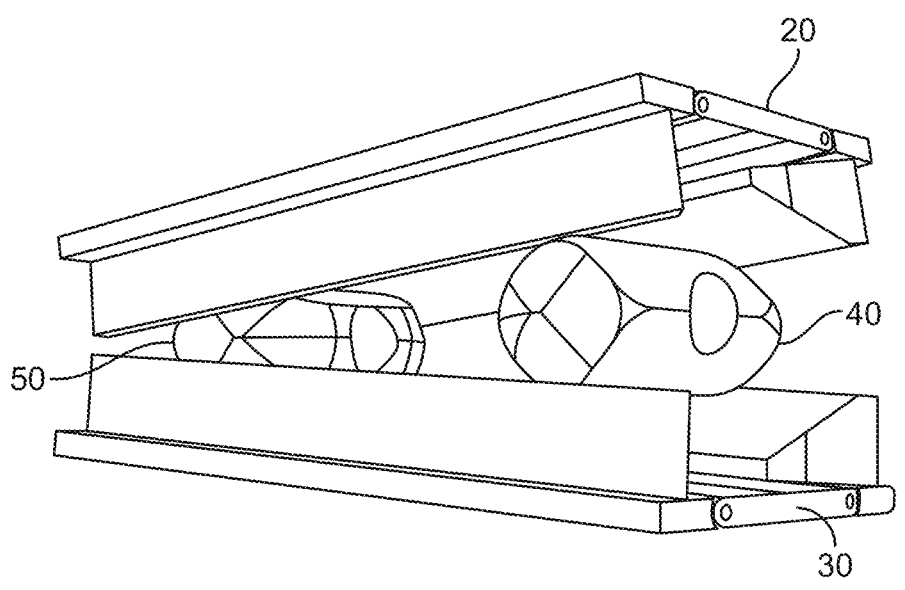
FIG. 7 is a perspective view of the present intervertebral cage showing deployment with the top and bottom plates angled to one another at a preferred lordotic angle.
Figure 8:
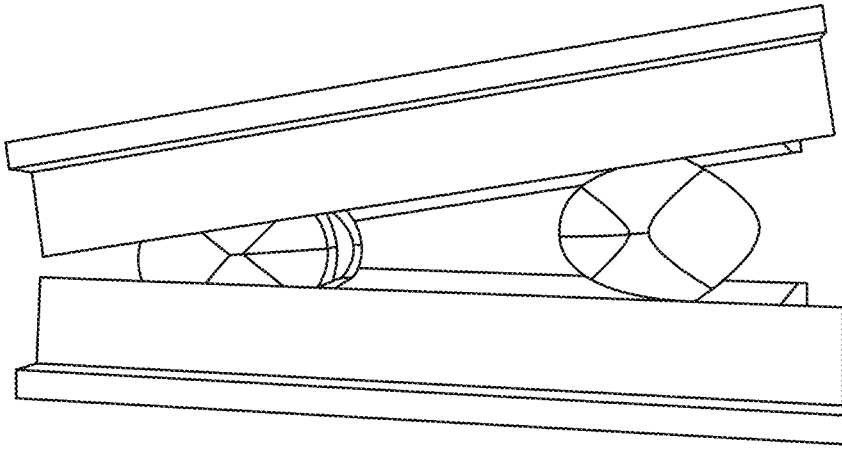
FIG. 8 is a side elevation view corresponding to FIG. 7.

As seen in FIGS. 7 and 8, moving one of the wedges (e.g.: front wedge 40) while keeping the other wedge (i.e.: rear wedge 50) stationary changes the angle of the top and bottom plates 20 and 30 with respect to one another, thereby varying a lordosis angle for the intervertebral cage.

Figure 9:
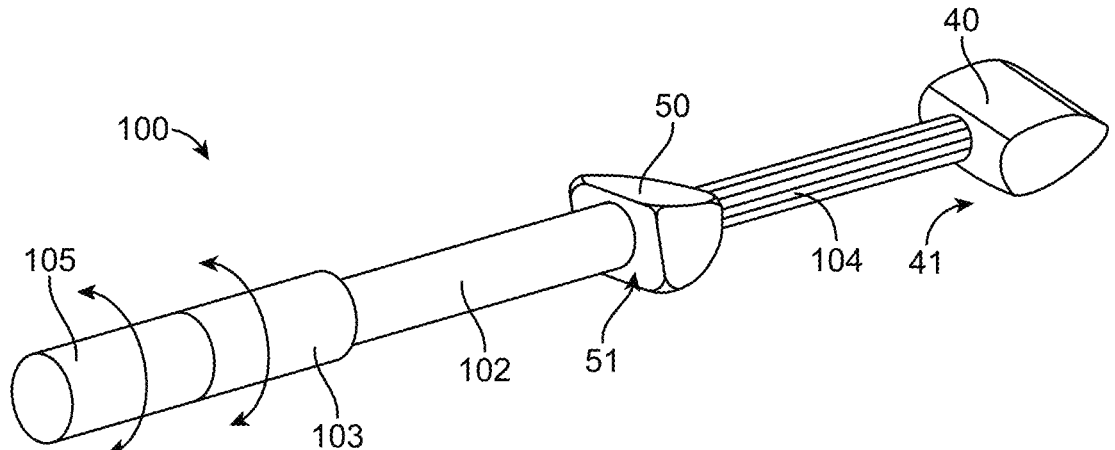
FIG. 9 is a perspective view of a deployment mechanism including a screw driver-type device for separately adjusting screw mechanisms on the front and rear wedges.
Figures 10, 11:
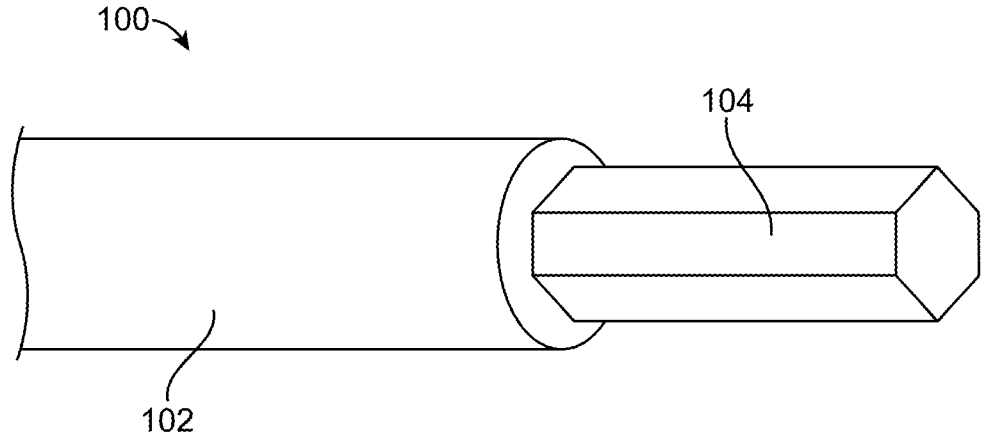
FIG. 10 is a perspective view of the distal end of the screw driver-type device of FIG. 9.
FIG. 11 is an elevation view of the distal end of the screw driver-type device of FIGS. 9 and 10.

FIGS. 9, 10 and 11 show a preferred screw driver-type device 100 that comprises an outer shaft 102 and an inner shaft 104. Inner shaft 104 is rotatable within outer shaft 102. By turning handle portion 103, an operator can rotate outer shaft 102. By rotating handle portion 105, an operator can rotate inner shaft 104.

Figure 12A:
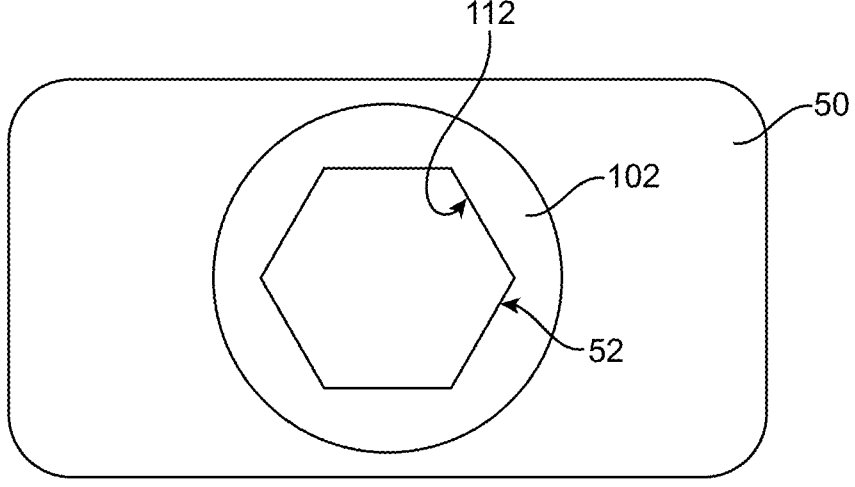
FIG. 12A is an illustration of the operation of the screw mechanism on the rear wedge.
Figure 12B:
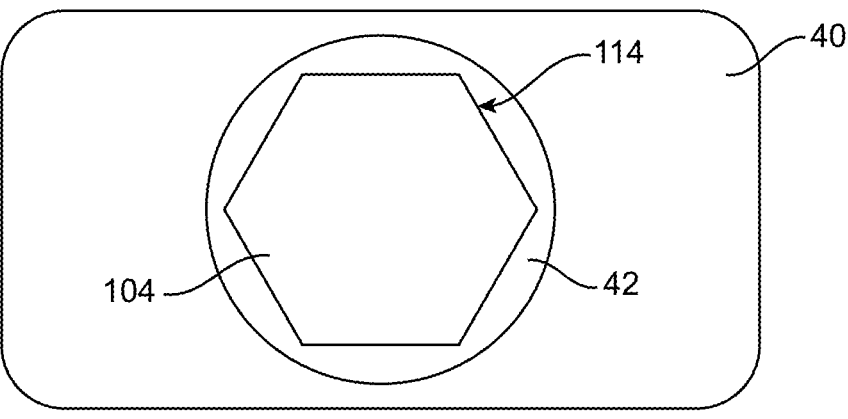
FIG. 12B is an illustration of the operation of the screw mechanism on the front wedge.

As seen in FIG. 12A, outer shaft 102 has an inner female portion 112 that mates with the outside surface of screw mechanism 52. As such, rotation of outer shaft 102 rotates the screw mechanism on rear wedge 50, thereby moving the rear wedge 50 forwards. As seen in FIG. 12B, inner shaft 104 has an outer male portion 114 that mates with the inside surface of screw mechanism 42. As such, rotation of inner shaft 104 rotates the screw mechanism on front wedge 40, thereby moving front wedge 40 backwards.

The present system also includes a preferred method of deploying an intervertebral cage in an intervertebral space, by: inserting an expandable intervertebral cage 10 into an intervertebral space, and then engaging a deployment mechanism 42 or 52 to move either or both of the front or rear wedges 40 and 50 to rotate the leaves 22 and 32 on the top and bottom plates 20 and 30 into their deployed positions. Optionally, this preferred method also includes moving the front and rear wedges 40 and 50 independently to vary a lordosis angle for the intervertebral cage.

Preferably as well, this method includes moving either or both of the front or rear wedges 40 and 50 to push against one or more blocks 21 and 31 disposed within the intervertebral cage, wherein each of the blocks 21 and 31 are positioned against one of the leaves 22 and 32 such that movement of the blocks moves the leaves into the deployed position, thereby increasing the width of the intervertebral cage. Optionally as well, the preferred method further comprises moving either or both of the front or rear wedges 40 and 50 to push against the blocks 21 and 31 such that the blocks move the top and bottom plates 20 and 30 father apart, thereby increasing the height of the intervertebral cage. Engaging the deployment mechanism preferably comprises rotating a first diameter screw mechanism 42 to move the front wedge 40 and rotating a second diameter screw mechanism 52 to move the rear wedge 50. In further optional aspects, each of the wedges 40 and 50 may be replaced by a pair of wedges, or some other number of wedges.

In preferred aspects, the cage is inserted into the disc space using a posterior approach. In such approach, the space to place the cage is typically at most about 15 mm in medial to lateral dimension by 15 mm in superior to inferior. Unfortunately, the posterior disc height is rarely more than 8 mm in patients who need surgery, and the dilemma is that the anterior disc often will need to be 14-16 mm when restored to normal height. Operating under these conditions can be done but it risks injury.

Therefore, the idea of using expandable cages is that they can be placed when collapsed to 8 mm or so and then expanded to 16 mm in the disc space, minimizing the risk to the neural structures while allowing the maximum restoration of disc height. Unfortunately however, current designs are limited either in that they only expand in height or they expand both in height and width but their surface area does not increase and such expansion thereby leaves a void in the middle of the cage.

In optional preferred aspects, the cage can be 8 mm in height and 10 mm wide when collapsed. Each leaf 22 and 32 could optionally be 4 mm wide. As the wedges are moved to lift/deploy the leaves, the width could be increased from 10 mm to 18 mm (10 mm original cage width+4 mm left leaf+4 mm right leaf). If the cage is 30 mm long, the surface area would increase from 330 mm$^2$ to 540 mm$^2$. If the cage were 10 mm high when inserted, the width becomes 20 mm and the surface area increases to 600 mm$^2$. It is to be understood that other dimensions are also possible, all keeping within the scope of the present invention.

In other optional embodiments, the top plate 20 and the bottom plate 30 may be connected together at a central pivot connection that permits plates 20 and 30 to move only a short vertical distance apart from one another even while positioned parallel to one another. As such, this pivot connection would permit a limited range of vertical motion between the top and bottom plates 20 and 30.

What is claimed is:

1. An expandable intervertebral cage, comprising:
   a top plate;
   a pair of rotatable leaves on opposite sides of the top plate;
   a bottom plate;
   a pair of rotatable leaves on opposite sides of the bottom plate; and
   a deployment mechanism, wherein the deployment mechanism rotates the leaves on the top and bottom plates into a deployed position,
wherein the deployed position of the leaves on the top plate is coplanar with the top plate and the deployed position of the leaves on the bottom plate is coplanar with the bottom plate;
   a front wedge; and
   a rear wedge;
wherein the deployment mechanism moves either or both of the front or rear wedges to rotate the leaves on the top and bottom plates into the deployed position, and
wherein moving one of the wedges while keeping the other wedge stationary changes the angle of the top and bottom plates with respect to one another, thereby varying a lordosis angle for the intervertebral cage.

2. The intervertebral cage of claim 1, wherein the leaves rotate from a vertical non-deployed position to a horizontal deployed position.

3. The intervertebral cage of claim 1, wherein deploying the leaves on the top and bottom plates increases the width of the intervertebral cage.

4. The intervertebral cage of claim 1, wherein the deployment mechanism moves the front and rear wedges independently of one another.

5. The intervertebral cage of claim 1, wherein the deployment mechanism moves either or both of the front or rear wedges to push the top and bottom plates farther apart.

6. The intervertebral cage of claim 5, wherein moving the front and rear wedges towards the center of the intervertebral cage increases the height of the intervertebral cage.

7. The intervertebral cage of claim 1, further comprising:
   four blocks disposed within the intervertebral cage, wherein one of the four blocks is positioned adjacent to each of the four leaves, and wherein movement of the blocks moves the leaves into the deployed position.

8. An expandable intervertebral cage, comprising:
   a top plate;
   a pair of rotatable leaves on opposite sides of the top plate;
   a bottom plate;
   a pair of rotatable leaves on opposite sides of the bottom plate;
   a deployment mechanism, wherein the deployment mechanism rotates the leaves on the top and bottom plates into a deployed position;
   a front wedge; and
   a rear wedge;
wherein the deployment mechanism moves either or both of the front or rear wedges to rotate the leaves on the top and bottom plates into a deployed position; and
wherein the deployment mechanism moves the front and rear wedges independently of one another, and wherein the deployment mechanism comprises screw adjustment mechanisms having different diameters for separately moving each of the front and rear wedges.

9. An expandable intervertebral cage, comprising:
   a top plate;
   a pair of rotatable leaves on opposite sides of the top plate;
   a bottom plate;
   a pair of rotatable leaves on opposite sides of the bottom plate;
   a deployment mechanism, wherein the deployment mechanism rotates the leaves on the top and bottom plates into a deployed position;
   a front wedge; and
   a rear wedge;
wherein the deployment mechanism moves either or both of the front or rear wedges to rotate the leaves on the top and bottom plates into a deployed position further comprising:
   four blocks disposed within the intervertebral cage, wherein one of the four blocks is positioned adjacent to each of the four leaves, and wherein movement of the blocks moves the leaves into the deployed position, wherein the front and rear wedges have angled surfaces thereon, and wherein the blocks have angled surfaces thereon, and wherein the blocks are moved by the angled surfaces of the front and rear wedges pushing against the angled surfaces of the blocks.

10. The intervertebral cage of claim 9, wherein the front and rear wedges are angled inwardly towards the center of the intervertebral cage, and wherein the blocks are angled inwardly towards the center of the intervertebral cage.

\* \* \* \* \*